US005470576A

United States Patent [19]
Patel

[11] Patent Number: 5,470,576
[45] Date of Patent: Nov. 28, 1995

[54] PROCESS FOR PREPARING THE ALGINATE-CONTAINING WOUND DRESSING

[75] Inventor: Harish A. Patel, Norfolk, Mass.

[73] Assignee: The Kendall Company, Mansfield, Mass.

[21] Appl. No.: 130,814

[22] Filed: Oct. 4, 1993

Related U.S. Application Data

[62] Division of Ser. No. 894,966, Jun. 8, 1992, abandoned.

[51] Int. Cl.⁶ ................................................. A61L 15/00
[52] U.S. Cl. ...................... 424/445; 424/447; 427/389.9
[58] Field of Search ................................... 424/445, 447; 427/389.9; 602/48, 49; 604/304

[56] References Cited

U.S. PATENT DOCUMENTS

| | | | |
|---|---|---|---|
| 2,688,586 | 9/1954 | Eberl et al. | 167/84 |
| 4,214,582 | 7/1980 | Patel | 128/156 |
| 4,421,583 | 12/1983 | Aldred et al. | 156/167 |
| 4,562,110 | 12/1985 | Tong | 428/284 |
| 5,256,477 | 10/1993 | Mahoney | 428/283 |

*Primary Examiner*—Jyothsna Venkat
*Attorney, Agent, or Firm*—David J. Koris

[57] ABSTRACT

Disclosed is a wound dressing comprising an absorbent pad impregnated with an alginate for promoting wound healing and which upon contact with the wound will exhibit haemostatic properties, the absorbent pad being characterized as being soft and highly pliant.

4 Claims, No Drawings

PROCESS FOR PREPARING THE ALGINATE-CONTAINING WOUND DRESSING

This is a division of application Ser. No. 07/894,966, filed Jun. 8, 1992, and now abandoned.

BACKGROUND OF THE INVENTION

Algin is a material obtained from seaweed. It can be converted into alginic acid which is insoluble and soluble salts such as sodium alginate or insoluble salts such as calcium alginate can be obtained therefrom. Alginates are also readily available from pharmaceutical sources, most commonly as the salt form, e.g. sodium alginate.

The use of calcium and sodium alginate materials made into wool, gauze and the like in surgery and in the dressing of wounds has been well known for many years, having, for example, been reported in surgery annals as early as 1947. More recently, various alginate wound dressing products have become commercially available, mainly in the form of calcium alginate fibers.

For example, in the United Kingdom, where much of the technology had its origin, dressings were made by converting sodium alginate into calcium alginate and then processing the fiber into a nonwoven fabric, to be cut into size, packaged and sterilized.

UK-based research in the 60's and 70's showed that alginates such as those produced in the above manner, e.g. SORBSON, marketed by Steriseal, produced the ideal warm, moist environment for healing wounds, including long-standing infected ulcers. This was found to be due to the ability of the fiber to react with the wound exudate and form a gel which is absorbent but keeps the wound moist and which can be changed by washing the saturated dressing away with saline solution. As a result, newly formed tissue is said not to be disturbed.

KALTOSTAT, developed by BritCair, another British Company, is a calcium alginate fiber produced by a special wet-spinning process from a variety of seaweed selected for having the best type of molecular construction for alginate fiber. Supplied in the form of nonwoven wound dressings for the treatment of exudating wounds, the product is said to encourage the formation of controlled ion-active gel over the wound site which reacts with the sodium ions in exudate or blood to aid wound healing.

A dual-treatment product is also offered under the name KATOCARB in which the wound-contact layer is of a calcium alginate fiber to which is bonded a woven pad of activated charcoal, the outer layer being a nonwoven polyester/viscose. The product is intended for use on wounds that are complicated by a bacterial infection and offensive odors.

Windsor Laboratories, yet another UK company, has introduced a woven calcium alginate dressing for over the counter pharmacy sale only. Called STOP HEMO, the sodium alginate formed with the exchange of sodium ions in the blood for the calcium ions forms a gel which acts as a dressing, while the calcium ions are said to encourage clot formation.

While alginate fiber dressings such as the commercially available ones mentioned above are highly efficacious in wound management, they nevertheless suffer the disadvantage of requiring the clinician to physically remove the resulting gel with the body fluids physically by wiping or by flushing with saline.

Other forms of alginate dressings are also known in the art, as evidenced by the patent literature. While not intended to represent a full survey of the patent literature, the following patents may nevertheless be taken as being fairly illustrative of the state of the art.

U.S. Pat. No. 2,512,616 observes that alginates exist in several forms, but that fibrous forms are preferred for use in surgical dressings. Alginates woven into a gauze or in the form of loose wool similar to absorbent cotton are particularly identified as being useful.

U.S. Pat. No. 3,879,168 discloses a partially soluble alginic material in the form of a gauze or wool, suitable for the preparation of surgical dressings, based on an alginic acid and containing calcium, sodium and acid forms, e.g. in the ratio of 4:5:1 and characterized by a calcium content of 2 to 6 percent and a reaction pH of 4 to 7.

U.S. Pat. No. 4,837,024 teaches the healing of a surface wound can be promoted by contacting the wound surfaces with a suspension of particles of collagen and a glycosaminoglycan that is chemotactic of fiberblasts and/or endothelial cells. Typical glycosaminoglycans are said to include alginates most commonly available as the sodium salt.

U.S. Pat. No. 4,948,575 is directed to dimensionally stable alginate hydrogel foam wound dressings formed in place in the wound cavity or on the wound surface from a reactive composition that foams as it gels. As is disclosed, the hydrogel foam is formed by mixing together a first liquid component (Component A) comprising an aqueous suspension of particles of water-insoluble di- or trivalent metal salt and an effervescent compound which effervesces when reacted with an acid; and a second liquid component (Component B) comprising an aqueous solution of a biocompatible water-soluble acid, wherein at least one of the Components A and B further comprises water-soluble alginate dissolved therein.

In the BACKGROUND OF THE ART, the patentees discuss the alginate fiber dressings such as those commercially available ones mentioned above, noting that although the fibrous wound dressings perform well, they have many inherent disadvantages such as difficulty in handling, poor structural integrity and tendency to shed fibers when dry, skill required to apply the dressings to the wound, the handling problems being aggravated when one's fingers are not completely dry, etc. Additionally, the patentees note that because the alginate fibers are highly absorbent, dressings based upon high basis weight webs of the fibers are more likely to desiccate a wound if applied to the wound in a dry condition. The manufacturer of the [above-mentioned] KALOSTAT dressing avoids this problem by recommending that the dressing be moistened before application to the wound. Nonfibrous alginate wound dressings are also said to be known, as illustrated by U.S. Pat. No. 4,393,048 of Mason et al disclosing a wound dressing comprising a water-soluble hydrogel of alkali metal alginate and glycerine. Additionally, Swedish Patent Application Publication Number 424,956 published Aug. 23, 1982 was cited as disclosing a water-insoluble alginate hydrogel wound dressing.

British Patent Specification No. 629,419 discloses a haemostatic surgical dressing which is formed by impregnating a cotton gauze or other fibrous material with relatively large quantities of insoluble alginate.

British Patent Specification 1,329,693 also discloses a surgical dressing comprising an alginate as a haemostat, the alginate being combined with a specified water-soluble polymer, apparently to allow the alginate to be cast or spread in the form of a film, sheet or block. The advantage is said to be that the film, sheet, or block slowly dissolves in contact with a wound or burn to release the alginate which is then free to exhibit haemostatic properties.

British Patent Specification No. 1,394,742 teaches a surgical dressing material comprising a layer of knitted alginic gauze adhered to a layer of fibrous backing material, the alginic material being calcium alginate or calcium alginate in which part of the calcium content has been replaced by sodium to render the material more soluble in water (so-called "converted calcium alginate"). The preferred converted calcium alginate is said to have a calcium content of 3 to 5% by weight and a Ph not less than 4.

European Patent Application Number 87303252.8 (Publication Number 0 243 069) discloses a wound-contacting layer fixed to a substantially liquid-impermeable plastics backing layer, the wound-contacting layer being formed from an alginate, the backing layer extending beyond the edges of the wound-contacting layer to provide a marginal portion which is coated with adhesive. The alginate may, for example, be calcium alginate, silver alginate, zinc alginate, sodium alginate, or mixtures thereof, calcium alginate being particularly preferred. As disclosed, the alginate layer may conveniently be in the form of a pad of alginate fibers. The pad may be lightly bonded together to give a degree of integrity and resistance to delamination.

Of the various prior publications known to Applicant, perhaps the most relevant to the instant invention is UK Patent Application No. 8917154.0 (Publication No. 2,221, 620 A) of Johnson & Johnson.

According to the invention described and claimed therein, there is provided a wound dressing material comprising a fibrous substrate having a discontinuous coating of a pharmaceutically acceptable alginate deposited on a surface thereof. By applying the alginate coating directly to the surface of a fibrous substrate, it is stated that a very large surface area of alginate in relation to its weight can be achieved. Effective homeostasis can therefore be obtained with relatively small amounts of alginate.

The alginate coating may comprise any pharmaceutically acceptable cationic alginate, such as sodium, calcium, potassium and ammonium alginates or mixtures thereof, sodium and calcium alginates and their mixtures being said to be preferred.

As is further stated in the aforementioned UK Application of Johnson & Johnson:

"Since it is not desired to form a continuous film of alginate on the substrate, there is no need to include film-forming water-soluble polymers in the alginate coating. Indeed, it is preferred that the alginate coating contain less than 40% by weight of other polymers, and more preferably less than 15% by weight. It is particularly preferred that no more than 5% by weight of other polymers be included in the alginate coatings, because their presence may interfere with the haemostatic effect of the alginate."

"In the absence of substantial quantities of a film-forming polymer, alginates tend to be rather friable, and the alginate coating in the wound dressing material for the present invention therefore preferably also contains a plasticizer such as ethylene glycol, propylene glycol or hexylene glycol, or an alkyl citrate or an appropriate mixture. The preferred plasticizer is glycerol (propan-1,2,3-triol). The plasticizer may constitute from 0% to 80% by weight of the coating, and preferably from 10 to 70% by weight. It is particularly preferred that the plasticizer be present in the coating in amount between 30 and 60% by weight."

"The alginate coating may optionally incorporate other additives such as antiseptics, analgesics or other medicaments, preferably in amounts less than 5% by weight, more preferably less than 2% by weight, and most preferably less than 1% by weight."

"When an alginate coating is applied to a fibrous substrate in accordance with the invention, the individual fibers which lie close to the surface of the substrate are at least partly coated. Also, extremely thin films of alginate may be formed between adjacent fibers near points of crossover. A discrete film or layer of alginate on the surface of the substrate is avoided, so that the permeability of the substrate to gases (such as air and water vapour) is not lost . . . "

"The alginate is preferably applied to the substrate as a viscous aqueous, or substantially aqueous, fluid. The viscosity of the aqueous suspension of the alginate composition may be adjusted to suit the coating technique employed . . . "

"The wound dressing materials of the present invention are suitable for use in a variety of forms. For example, they may be used either alone (being secured in place by bandaging, adhesive tape, or any other suitable means), or they may be formed into composite dressings. Indeed, the material of the present invention can advantageously be used in any of the circumstances in which absorbent wound dressing pads are conventionally used. They are particularly suitable for use as post-operative dressings."

"Composite dressings including the dressing material of the present invention will generally comprise a fibrous pad having an alginate coating on one surface, and a backing material secured to the opposed surface. The backing material may be porous or non-porous, but materials which are impermeable to water but permeable to water vapour are particularly preferred. Such materials include, for example, cast polyurethane films. Alternatively, the backing material may be a perforated plastics film, such as those conventionally used in first-aid dressings."

Neither Applicant nor its corporate assignee, the Kendall Company which has a substantial business in wound care, has any knowledge of commercial exploitation of the above-described Johnson & Johnson alginate dressing.

In any case, it will be seen that the published UK application, substantial portions of which has been described above, teaches that the composition for coating the dressing should contain, in addition to the cationic alginate, a plasticizer as well as a viscosity adjuster to facilitate coating. Additionally, as disclosed on page 5 of the application, if a sodium/calcium alginate coating is required, a viscous aqueous solution of sodium alginate can be prevented from forming an immediate gel in the presence of calcium ions by the inclusion of pH controlling materials such as glucono lactone or adipic acid/sequestering agent.

Apart from the added manufacturing cost of including such reagents which have no beneficial effect on wound care, it will be appreciated that federal drug regulations may require biocompatability data showing that these additives cause no adverse effects, whether topically or systemically by transdermal diffusion, thereby complicating approval for marketing.

Stated simply, the task of the present invention is to provide an alginate-containing wound dressing which exhibits haemostatic properties, the dressing being characterized as being soft and highly pliant and being manufactured in an elegant and cost-effective manner which does not require the presence in the dressing of any chemicals other than the desired alginate for promoting wound healing.

BRIEF DESCRIPTION OF THE INVENTION

In accordance with this invention, the task is solved simply and efficiently by providing an alginate wound dressing comprising an absorbent pad, e.g. a dry woven or nonwoven fabric impregnated with calcium alginate or a mixture of calcium and sodium alginate.

An important feature of the present invention is the step of mechanically softening the impregnated dressing, as will be described in detail hereinafter.

DETAILED DESCRIPTION OF THE INVENTION

As was heretofore alluded to, the present invention is directed to absorbent dressings impregnated with calcium alginate or a mixture of calcium and sodium alginate in order to incorporate the per se known advantages of alginates in promoting wound healing into the well known absorbent dressings.

In its simplest form, the wound dressings of this invention will comprise an absorbent woven or nonwoven fabric made from any of the materials which were heretofore employed in dressings to receive and absorb wound fluids. By way of illustration, mention may be made of fibers of cotton/polyolefin, cotton/polyester and rayon/polyester blends, cotton, rayon, cellulosic materials, etc. In accordance with this invention the absorbent pad will appear to the eye and to the touch to be the same as any of the conventional absorbent pads, except that, in accordance with this invention the pad will be impregnated with calcium alginate or a mixture of calcium and sodium alginate. Such mixtures are known in the art and commercially available. They may also be prepared by what has heretofore been termed "converted calcium alginate", namely, an alginic material where a part of the calcium content has been replaced by sodium to render the material more soluble in water.

Specifically, the wound dressings of this invention will contain at least about 5% by weight of calcium alginate based upon the total alginate content. Stated another way, in accordance with this invention, the wound dressings contemplated by this invention will contain from about 5 to 100 parts by weight of calcium alginate and from 0 to 95 parts by weight of sodium alginate. Where a mixture of sodium and calcium alginate is contemplated, a preferred ratio is on the order of 68 part by weight of sodium alginate and 32 parts by weight of calcium alginate, i.e. a 68/32 Na/Ca mixture.

Where it is desired for the alginic content to be 100% calcium alginate, the absorbent pad may be prepared by the steps of: (1) impregnating the pad with an aqueous solution of sodium alginate, e.g. by dipping the pad into an aqueous bath containing 1–10% sodium alginate; (2) removing the pad from the bath; (3) introducing the thus impregnated pad into an aqueous bath containing 1–10% calcium chloride to convert the sodium alginate to calcium alginate; (4) removing the pad now impregnated with calcium alginate and squeezing off excess liquid; (5) preferably washing with deionized water; (6) drying, for example, by passing between heated rollers; and thereafter (7) softening mechanically to provide the finished alginate-impregnated absorbent dressing.

The mechanical softening is preferably accomplished by the process known in the art as "micrexing", using a commercially available "MICREX" system of the type described in U.S. Pat. Nos. 3,260,778 or 3,426,405, which system may, for example, be obtained from the Micrex Division of Bird Machine Company. The micrexing system, sometimes also referred to in the art as "micropleating" or "microcreping", applies longitudinal compressive forces as the fabric passes through the nip of superposed rolls operating at different speeds, thereby producing a condensed micropleated texture web to provide a fabric that has a plurality of small discontinuous pleats extending across the fabric. The resulting fabric is characterized as being flexible and soft. While it is extensible in the lengthwise direction (transverse to the pleats), it is not elastic since, once extended, it does not return to its compacted length. As illustrative of the patent literature employing micrexing, mention may be made of U.S. Pat. Nos. 2,761,490; 2,915,109; 3,066,046; 3,220,056; 3,754,289; 4,555,811; and 4,606,338. Accordingly, since micrexing is so well known in the art, it need not be described in more detail for a clear understanding of the present invention.

In the process just described, the alginic content in the absorbent pad will be substantially 100 percent calcium alginate. In the preferred embodiment of this invention, however, the alginic content will consist of a mixture of calcium alginate and sodium alginate, most preferably a mixture wherein the percentage by weight of sodium alginate to calcium alginate, based upon the total weight of the mixture is from about 60 Na/40 Ca to about 70 Na/30 Ca.

The preferred wound dressings containing a mixture of sodium and calcium alginate may be prepared by the steps of (1) first coating a converted calcium alginate containing the desired proportions of sodium and calcium alginate with a small amount of an organic water-miscible solvent such as ethyl alcohol so as to prevent it from gelling immediately on contact with water; (2) adding deionized or distilled water; (3) impregnating the gauze pad with the thus formed alginate solution by immersing the gauze pad in the solution; (4) removing the gauze pad, squeezing off excess liquid and drying, e.g. by passing between heated rollers; and (5) thereafter softening mechanically to provide the finished alginate-impregnated absorbent dressing.

The alginate wound dressings of this invention may be prepared by batch or continuous processing. In the latter, a moving web of the fabric to be impregnated may be advanced to various stations to carry out the above-mentioned steps and then wound on a take-up roll. It may then be subjected to the slitting and cutting steps to provide dressings of the desired dimensions at the same location or stored and/or transported to a different location for slitting and cutting. After packaging and sterilizing, the alginate dressing is ready for shipment and use.

In each of the above-mentioned alternatives, the novel wound dressings of this invention are characterized as comprising a soft, highly pliant fabric pad impregnated with an "effective amount" of calcium alginate alone or in admixture with sodium alginate. As used herein, the term "effective amount" means an amount sufficient to provide haemostatic properties by means of ion exchange with blood and to provide a moist environment promoting wound healing. By way of illustration, the ratio by weight of the impregnated fabric to the weight of the alginate impregnated therein may be on the order of from about 4:1 to about 8:1. Lesser amounts of alginate will provide at least some beneficial results and are accordingly considered to provide the utility contemplated for this invention; while greater amounts may provide no added benefits.

While the alginate may be considered to be the effective ingredient for use in the practice of this invention, it will be appreciated that the dressing may, if desired, contain other reagents performing specific desired functions. As examples of such additional reagents heretofore incorporated into wound dressings, mention may be made of bactericides, fungicides, bleaches, stabilizers, viscosity modifiers and the like.

As was heretofore alluded to, in its simplest form, the alginate dressings of this invention will consist simply of an impregnated pad which may be applied to the wound and, if desired, held in place on the skin with pressure-sensitive adhesive strips in per se known manner.

However, more sophisticated dressings embodying this invention are also contemplated.

For example, it is envisioned that an alginate wound dressing of this invention may comprise two separate but contiguous fabrics, e.g. a high density woven or nonwoven fabric having optimum spreading or wicking characteristics and impregnated with alginate as heretofore described; and a contiguous low density fabric having optimum absorption capacity. The high density fabric may have a density of on the order of 0.1 to 0.2 gm/(cm)$^3$; while the low density fabric will have a density less than 0.1, e.g. on the order of 0.05 gm/(cm)$^3$. A dressing of this description will optimize the ability of the dressing to receive and absorb wound fluids. Alternatively, the alginate-impregnated pad may be used in combination with a hydrogel or hydrocolloid layer for receiving and retaining large amounts of wound exudate diffusing to it through the alginate pad.

Like other known wound dressings, including those commercially available, the wound dressings contemplated by this invention may be carried on a cover or backing sheet, preferably one which is liquid- and bacteria-impermeable, e.g. polyurethane, a polyolefin such as polyethylene or polypropylene, a polyester such as polyethylene terephthalate, etc. If the cover sheet and the dressing fabric have a common periphery, it will be appreciated that adhesive strips will be required to secure the dressing to the skin covering the wound. However, the backing sheet may be of somewhat larger dimensions and carry a layer of pressure sensitive adhesive to which the dressing is substantially centrally disposed, thereby leaving a peripheral adhesive area surrounding the dressing for securing it to the skin.

Since it is to be expressly understood that the invention is in general applicable to the per se known wound dressing structures including a gauze pad or the like for placement on the wound, it will be appreciated that various other modifications in structure per se comprise no part of this invention. For this reason, such modifications need not be discussed further. Accordingly, it will be appreciated that the particular form of the alginate dressings contemplated by this invention are considered to be a matter of individual choice or whim within the expected judgment of the skilled worker in the light of the foregoing description.

The following examples show by way of illustration and not by way of limitation the practice of this invention.

EXAMPLE 1

To 10.0 cc of ethyl alcohol were added with stirring 2.0 grams of sodium alginate and 1.0 gram of a bleach, sodium hypochlorite. 100 grams of deionized water were then added and the resulting mixture was allowed to sit for approximately 24 hours. A gauze pad was immersed into the mixture for a few seconds, then removed and quickly immersed in a aqueous 5% calcium chloride bath to convert the sodium alginate to calcium alginate. It was then removed, excess liquid squeezed off and washed with distilled water. After washing, the wet pad now impregnated with calcium alginate was dried by passing between heated rollers at a temperature on the order of 140° F. The dried pad, which was stiff and rather inflexible, was then micrexed in known manner to provide a soft and highly pliant dressing impregnated with calcium alginate.

EXAMPLE 2

To 10.0 cc of ethyl alcohol were added with stirring 2.0 grams of a converted calcium alginate consisting of 68% by weight of sodium alginate and 32% by weight of calcium alginate, along with 1.0 gm of glycerin as wetting agent. 100 grams of deionized water were then added with stirring and the mixture was allowed to sit for about 24 hours. A gauze pad was then immersed in the mixture to impregnate the pad with the converted calcium alginate mixture. Unlike the previous example, no further chemical treatment was required. The impregnated pad was then dried and micrexed as in the previous example to provide an alginate dressing which, like the previous example, was characterized as being soft and highly pliant.

Since certain changes may be made without departing from the scope of the invention herein contemplated, it is to be understood that the foregoing description, including the examples, shall be taken as illustrative and not in a limiting sense.

What is claimed is:

1. A process for preparing a wound dressing containing calcium alginate consisting of the steps of impregnating an absorbent fabric with an aqueous solution of sodium alginate; thereafter introducing the sodium alginate-impregnated fabric into an aqueous solution of calcium chloride to convert the sodium alginate to calcium alginate; washing the calcium alginate-containing fabric with deionized water; drying the calcium alginate-containing fabric; and thereafter mechanically softening the fabric to provide a soft, highly pliant wound dressing.

2. A process as defined in claim 1 wherein the mechanical softening is effected by micrexing wherein longitudinal compressive forces are applied to the fabric as the fabric passes through the nip of superposed rolls operating at different speeds, thereby producing a condensed micropleated texture web to provide a fabric having a plurality of small discontinuous pleats extending across the fabric.

3. A process for preparing an alginate-containing wound dressing comprising the steps of:

coating a mixture of sodium and calcium alginate with ethyl alcohol to prevent the alginate from gelling immediately on contact with water;

thereafter adding deionized or distilled water to the ethyl alcohol-coated alginate mixture to form an alginate solution;

impregnating a woven or nonwoven fabric with the alginate solution;

drying the fabric impregnated with the mixture of sodium and calcium alginate; and thereafter mechanically softening the fabric to provide a soft, pliant wound dressing.

4. A process as defined in claim 3 wherein the mechanical softening is effected by micrexing wherein longitudinal compressive forces are applied to the fabric as the fabric passes through the nip of superposed rolls operating at different speeds, thereby producing a condensed micropleated texture web to provide a fabric having a plurality of small discontinuous pleats extending across the fabric.

\* \* \* \* \*